(12) United States Patent
Bai et al.

(10) Patent No.: US 12,667,645 B2
(45) Date of Patent: Jun. 30, 2026

(54) IONIC POLYMERS FOR MEDICAL DEVICE APPLICATIONS

(71) Applicant: Becton, Dickinson and Company, Franklin Lakes, NJ (US)

(72) Inventors: He Bai, Sandy, UT (US); James Joseph Semler, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 816 days.

(21) Appl. No.: 17/991,938

(22) Filed: Nov. 22, 2022

(65) Prior Publication Data

US 2023/0166001 A1     Jun. 1, 2023

Related U.S. Application Data

(60) Provisional application No. 63/284,059, filed on Nov. 30, 2021.

(51) Int. Cl.

| | |
|---|---|
| *A61L 27/26* | (2006.01) |
| *A61L 27/54* | (2006.01) |
| *C09D 123/06* | (2006.01) |
| *C09D 127/18* | (2006.01) |
| *C09D 133/02* | (2006.01) |
| *C09D 175/04* | (2006.01) |

(52) U.S. Cl.
CPC .............. *A61L 27/26* (2013.01); *A61L 27/54* (2013.01); *C09D 123/06* (2013.01); *C09D 127/18* (2013.01); *C09D 133/02* (2013.01); *C09D 175/04* (2013.01); *A61L 2300/206* (2013.01); *A61L 2300/404* (2013.01); *A61L 2300/42* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 3,755,218 A | 8/1973 | Yen et al. | |
| 3,853,804 A | 12/1974 | Yen et al. | |
| 4,642,267 A | 2/1987 | Creasy et al. | |
| 4,664,259 A | 5/1987 | Landis | |
| 4,713,402 A | 12/1987 | Solomon | |

(Continued)

FOREIGN PATENT DOCUMENTS

| | | |
|---|---|---|
| GB | 2239604 A | 7/1991 |
| WO | 2018140911 A1 | 8/2018 |
| WO | 2022182971 A1 | 9/2022 |

OTHER PUBLICATIONS

Functional Modification of Biomaterials to Manage Microbial Biofilm Formation, Sun, Xinbo, Nov. 4, 2012, pp. 1-193, ProQuest LLC. (Year: 2012).*

(Continued)

*Primary Examiner* — Peter A Salamon
(74) *Attorney, Agent, or Firm* — SERVILLA WHITNEY LLC

(57) ABSTRACT

Medical articles formed from ionically bonding an ionic polymer and an active agent provide enhanced properties. The ionic polymer may be one or more of an anionic polymer, a cationic polymer, and a zwitterionic polymer. The device may also include a nonionic polymer. Medical articles herein have antimicrobial, anti-fouling, and/or anti-thrombotic characteristics.

17 Claims, 4 Drawing Sheets

(56)  References Cited

U.S. PATENT DOCUMENTS

| | | | | |
|---|---|---|---|---|
| 4,834,702 | A | * | 5/1989 | Rocco ................... A61B 17/22 |
| | | | | 251/4 |
| 5,061,254 | A | | 10/1991 | Karakelle et al. |
| 5,147,319 | A | | 9/1992 | Ishikawa et al. |
| 5,159,050 | A | | 10/1992 | Onwumere |
| 5,322,659 | A | | 6/1994 | Walder et al. |
| 5,525,348 | A | | 6/1996 | Whitbourne et al. |
| 5,693,022 | A | | 12/1997 | Haynes |
| 6,261,271 | B1 | | 7/2001 | Solomon et al. |
| 6,413,243 | B1 | | 7/2002 | Geist |
| 6,866,859 | B2 | | 3/2005 | Trogolo et al. |
| 9,314,407 | B2 | | 4/2016 | Blizzard et al. |
| 9,561,309 | B2 | | 2/2017 | Glauser et al. |
| 9,675,717 | B2 | | 6/2017 | Kim et al. |
| 9,895,470 | B2 | | 2/2018 | Li et al. |
| 2004/0106912 | A1 | * | 6/2004 | Rosinskaya ........... A61L 29/085 |
| | | | | 604/500 |
| 2009/0263431 | A1 | * | 10/2009 | Fugmann .............. A61L 15/225 |
| | | | | 514/635 |
| 2011/0144577 | A1 | * | 6/2011 | Stankus ................... A61P 9/10 |
| | | | | 514/291 |
| 2013/0216599 | A1 | | 8/2013 | Kumar et al. |
| 2015/0151054 | A1 | | 6/2015 | Wilkinson |
| 2016/0038648 | A1 | * | 2/2016 | Gemborys .............. A61L 31/10 |
| | | | | 623/1.42 |
| 2018/0105665 | A1 | | 4/2018 | Day et al. |
| 2019/0175794 | A1 | * | 6/2019 | Meng ................... A61L 29/085 |

OTHER PUBLICATIONS

Non-Final Office Action in U.S. Appl. No. 17/991,937 dated May 21, 2025, 18 pages.
PCT International Search Report and Written Opinion in PCT/US2022/080679 dated May 9, 2023, 28 pages.
PCT International Search Report and Written Opinion in PCT/US2022/080680 dated May 22, 2023, 28 pages.
PCT Invitation to Pay Additional Fees in PCT/US2022/080679 dated Mar. 15, 2023, 23 pages.
Francolini, I. , et al., "Polyurethane anionomers containing metal ions with antimicrobial properties: Thermal, mechanical and biological characterization", Acta Biomaterialia, Elsevier, Amsterdam, NL, vol. 6, No. 9, Sep. 1, 2010 (Sep. 1, 2010) , pp. 3482-3490, XP027170162, ISSN: 1742-7061.
Richey, T. , et al., "Surface modification of polyethylene balloon catheters for local drug delivery", Biomaterials, vol. 21, Jan. 1, 2000 (Jan. 1, 2000), pp. 1057-1065.
Sun, Xinbo , "Functional Modification of Biomaterials to Manage Microbial Biofilm Formation", Nov. 4, 2012 (Nov. 4, 2012) , pp. 1-193.
Edwards Lifesciences Receives FDA Clearance To Market Its Vantex Central Venous Catheter, Edwards Lifesciences, https://www.edwards.com/ns20000621.
Harland Coating Chemistries, Lubricious Hydrophilic Coatings & more, https://harlandmedical.com/products/materials/#antimicrobial-coatings.
Technology—LiquiGlide's permanently wet surface, https://liquiglide.com/tech/.

"A Global Provider of Medical Technologies", Teleflex, https://www.teleflex.com/la/en/product-areas/vascular-access/central-venous-catheters/.
"Astute® Enhanced Lubricious Coating", BioInteractions, https://biointeractions.com/products_astute.php.
"AvertPlus™ Antimicrobial Coating", BioInteractions, https://biointeractions.com/products_avertplus.php.
"Micro Surfaces for Medical Devices", Hoowaki.
"New PICC Mimics Nature", https://www.prweb.com/releases/r4_vascular/biomimetic/prweb2596764.htm.
"PALINDROME™ Precision Chronic Hemodialysis Catheters", https://www.medtronic.com/covidien/en-us/products/dialysis-access/chronic-vascular/palindrome-catheters.html.
"The Story of Endexo Anti-Thrombotic Polymer Additives from Interface Biologics", Medical Plastics News,https://www.medicalplasticsnews.com/news/medical-plastics-technology-news/the-story-of-interface-biologics/.
"What is CovaCoat®?", Covalon Technologies Ltd (http: / /www.covalon.com).
Begovac, P. C., et al., "Improvements in GORE-TEX1 Vascular Graft Performance by Carmeda1 BioActive Surface Heparin Immobilization", Eur J Vasc Endovasc Surg 25, 432±437 (2003).
Colletta, Alessandro , et al., "S-Nitroso-N-acetylpenicillamine (SNAP) Impregnated Silicone Foley Catheters: A Potential Biomaterial/Device To Prevent Catheter-Associated Urinary Tract Infections", ACS Biomater. Sci. Eng. 2015, 1, 416-424.
Hazan, Zadik , et al., "Effective Prevention of Microbial Biofilm Formation on Medical Devices by Low-Energy Surface Acoustic Waves", Antimicrobial Agents and Chemotherapy, Dec. 2006, p. 4144-4152, vol. 50, No. 12.
Jamal, Mohamed A., et al., "In Vivo Biocompatibility and In Vitro Efficacy of Antimicrobial Gendine-Coated Central Catheters", Antimicrobial Agents and Chemotherapy, Sep. 2015 vol. 59 No. 9.
Kurt, Pinar , et al., "Highly Effective Contact Antimicrobial Surfaces via Polymer Surface Modifiers", Langmuir 2007, 23, 4719-4723.
Kushwaha, Meenakshi , et al., "A nitric oxide releasing, self assembled peptide amphiphile matrix that mimics native endothelium for coating implantable cardiovascular devices", Biomaterials 31 (2010) 1502-1508.
Liu, Hanyang , et al., "Auranofin Releasing Antibacterial and Antibiofilm Polyurethane Intravascular Catheter Coatings", Frontiers in Cellular and Infection Microbiology, Feb. 2019, vol. 9, Article 37.
Pathak, Rahul , et al., "Inhibition of bacterial attachment and biofilm formation by a novel intravenous catheter material using an in vitro percutaneous catheter insertion model", Medical Devices: Evidence and Research 2018:11 427-432.
Shehatou, Cindy , et al., "Characterizing the Antimicrobial Properties of 405nm Light and the Corning® Light-Diffusing Fiber Delivery System", Lasers in Surgery and Medicine Published by Wiley Periodicals, Inc.
Sotiri, Irini , et al., "Immobilized liquid layers: A new approach to anti-adhesion surfaces for medical applications", Experimental Biology and Medicine 2016; 241: 909-918. DOI: 10.1177/1535370216640942.

* cited by examiner

IONIC POLYMERS FOR MEDICAL DEVICE APPLICATIONS

CROSS-REFERENCE TO RELATED APPLICATIONS

This application claims priority under 35 U.S.C. § 119(e) to U.S. Provisional Application No. 63/284,059, filed Nov. 30, 2021, the disclosure of which is incorporated herein by reference in its entirety.

TECHNICAL FIELD

Embodiments of the disclosure generally relate to medical devices and methods of manufacture. More particularly, embodiments of the disclosure are directed to medical devices having ionic polymers ionically bonded to an active agent. The active agent may be an antimicrobial agent and/or an antithrombogenic agent.

BACKGROUND

Infusion therapy medical devices, such as syringe cannulas and catheters used for sampling or medicament administration, typically have components that are in direct contact with infusion fluid and/or bodily fluid that can cause infection. For example, catheter-related bloodstream infections may be caused by colonization of microorganisms, which can occur in patients whose treatment includes intravascular catheters and I.V. access devices. These infections can lead to illness and excess medical costs. Impregnating and/or coating catheters and I.V. access devices with various antimicrobial agents (e.g., chlorhexidine, silver, or other antibiotics) is a common approach that has been implemented to prevent these infections.

Some blood contact devices have the potential to generate thrombus. When blood contacts a foreign material, a complex series of events occur. These involve protein deposition, cellular adhesion and aggregation, and activation of blood coagulation schemes. Thrombogenicity has conventionally been counteracted by the use of anticoagulants, such as heparin. Attachment of heparin to otherwise thrombogenic polymeric surfaces may be achieved with various surface coating techniques.

Impregnating catheters and/or I.V. access devices directly with antimicrobial and/or antithrombogenic agents does not create chemical bonding between active agents and polymer substrates, thus devices would lose antimicrobial/antifouling efficacy in a short time.

On the other hand, surface coating techniques are to stabilize (chemically or physically) antimicrobial and/or antithrombogenic agents onto surface of the polymer substrate to achieve non-leaching or controlled release of such active agents. However, these coating techniques normally require priming of polymer substrates (e.g., chemical or plasma treatments), followed by multiple surface coating steps, which would complicate the medical device manufacturing process and significantly increase manufacturing costs.

Thus, there is a need for medical devices that can bond and demonstrate controlled release of antimicrobial and/or antithrombogenic agents to achieve antimicrobial and/or anti-fouling characteristics for an extended period of time.

SUMMARY

One or more embodiments are directed a medical device comprising: an ionic polymer ionically bonded to an active agent, the ionic polymer comprising one or more of an anionic polymer, a cationic polymer, and a zwitterionic polymer; and an optional nonionic base polymer, wherein the anionic polymer comprises a functional group selected from one or more of carboxylate ($-COO^-$), sulfonate ($-SO_3^-$), organosulfate ($-O-SO_3^-$), organophosphate ($-O-PO_3^-R^1$ or $-O-PO_3^{2-}$), phenolate ($-C_6H_4-O^-$), and thiolate ($-S^-$), wherein the cationic polymer comprises a functional group selected from one or more of phosphonium ($-P^+(R^1)(R^2)(R^3)$), imidazolium, pyridinium, sulfonium, guanidinium, thiazolium, and quinolinium, or wherein the cationic polymer comprises two or more functional groups selected from quaternary ammonium ($-N^+(R^1)(R^2)(R^3)$), phosphonium ($-P^+(R^1)(R^2)(R^3)$), imidazolium, pyridinium, sulfonium, guanidinium, thiazolium, and quinolinium, wherein the zwitterionic polymer comprises two or more functional groups selected from carboxylate ($-COO^-$), sulfonate ($-SO_3^-$), organosulfate ($-O-SO_3^-$), organophosphate ($-O-PO_3^-R^1$ or $-O-PO_3^{2-}$), phenolate ($-C_6H_4-O^-$), thiolate ($-S^-$), quaternary ammonium ($-N^+(R^1)(R^2)(R^3)$), phosphonium ($-P^+(R^1)(R^2)(R^3)$), imidazolium, pyridinium, sulfonium, guanidinium, thiazolium, and quinolinium, and wherein $R^1$, $R^2$, and $R^3$ independently comprise hydrogen, halogen, alkyl, and aryl.

An additional embodiment is directed to method of manufacturing a medical device, the method comprising: ionically bonding an ionic polymer and an active agent, and, optionally, a nonionic base polymer, the ionic polymer comprising one or more of an anionic polymer, a cationic polymer, and a zwitterionic polymer, wherein the anionic polymer comprises a functional group selected from one or more of carboxylate ($-COO^-$), sulfonate ($-SO_3^-$), organosulfate ($-O-SO_3^-$), organophosphate ($-O-PO_3^-R^1$ or $-O-PO_3^{2-}$), phenolate ($-C_6H_4-O^-$), and thiolate ($-S^-$), wherein the cationic polymer comprises a functional group selected from one or more of phosphonium ($-P^+(R^1)(R^2)(R^3)$), imidazolium, pyridinium, sulfonium, guanidinium, thiazolium, and quinolinium, or wherein the cationic polymer comprises two or more functional groups selected from quaternary ammonium ($-N^+(R^1)(R^2)(R^3)$), phosphonium ($-P^+(R^1)(R^2)(R^3)$), imidazolium, pyridinium, sulfonium, guanidinium, thiazolium, and quinolinium, wherein the zwitterionic polymer comprises two or more functional groups selected from carboxylate ($-COO^-$), sulfonate ($-SO_3^-$), organosulfate ($-O-SO_3^-$), organophosphate ($-O-PO_3^-R^1$ or $-O-PO_3^{2-}$), phenolate ($-C_6H_4-O^-$), thiolate ($-S^-$), quaternary ammonium ($-N^+(R^1)(R^2)(R^3)$), phosphonium ($-P^+(R^1)(R^2)(R^3)$), imidazolium, pyridinium, sulfonium, guanidinium, thiazolium, and quinolinium, and wherein $R^1$, $R^2$, and $R^3$ independently comprise hydrogen, halogen, alkyl, and aryl.

DETAILED DESCRIPTION

Figure 1:
FIG. 1 is a plan view of an exemplary medical device.

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

An ionic polymer is a polymer which contains both covalent bonds and ionic bonds in its molecular structure. The ionically charged functional group of an ionic polymer may include one or more of a cationic functional group and an anionic functional group to form one or more of a cationic polymer, an anionic polymer, or a zwitterionic polymer. Cationic polymers are macromolecules that have positive charges, which can be intrinsically present in the polymer backbone and/or in sidechains. Anionic polymers are macromolecules that have electronegative groups, which can be intrinsically present in the polymer backbone and/or in sidechains. Zwitterionic polymers are macromolecules that have both positive and negative charges incorporated into their polymer backbone and/or in sidechains.

An antimicrobial agent is a substance that kills microorganisms or stops their growth. Antimicrobial agents that can be used for bonding with cationic and/or anionic functional groups of the ionic polymer include any anionic antibiotics, e.g., cloxacillin salt, cefoxitin salt, cefazolin salt, penicillin salt, or derivatives thereof, and cationic antiseptics, e.g., chlorhexidine acetate, chlorhexidine gluconate, silver sulfadiazine, benzalkonium chloride, cetylpyridinium chloride, or derivatives thereof. In addition, quaternary ammonium-containing biocides, guanidine-containing biocides, cationic antimicrobial polymers, antimicrobial peptides or peptide-mimics, antifouling phospholipids or phospholipid-mimics, and derivatives thereof can also be ionically bonded with anionic functional groups of the ionic polymer to actively and/or passively provide advantages of enhanced surface properties including antimicrobial and/or anti-fouling.

An antithrombogenic agent is a substance which prevents the formation of a blood clot. Anionic antithrombogenic agents, e.g., heparin salt, or derivatives thereof can be ionically bonded with cationic functional groups of the ionic polymer to provide antithrombotic properties.

Moreover, the skilled artisan will recognize that anionic and/or cationic biocides and anticoagulants of either small molecules or macromolecules can also be used for bonding with cationic and/or anionic functional groups of the ionic polymer.

As used herein, the term "active agent" refers to an antimicrobial agent, an antithrombotic agent, or combinations thereof, which is an anionic, cationic, or zwitterionic compound that can bind to an ionic polymer. Accordingly, in some embodiments, the active agent provides antimicrobial activity, antifouling activity, or a combination thereof.

Principles and embodiments of the present disclosure relate generally to ionic polymer devices having improved properties, and methods of preparing and using them. Provided are medical articles, for example, catheter tubing, that have antimicrobial and/or anti-fouling characteristics by ionically bonding and stabilizing active agents to provide desirable material properties, including antimicrobial, anti-fouling, and/or antithrombogenicity. Provided are ionic polymers that are ionically bonded to antimicrobial/antithrombogenic agents to achieve controlled release of said antimicrobial/antithrombogenic agents from a medical device, e.g., catheter, extensions, IV tubing, catheter adapter, Luer port, connector body, device housing, a component thereof, combinations thereof, and the like, in order to prevent blood stream infections and blood clots, such as deep vein thrombosis (DVT) and thrombosis-induced catheter occlusions.

In FIG. 1, an exemplary medical device in the form of a catheter is illustrated. Tubing made from an ionic polymer ionically bonded to an active agent as disclosed herein forms the catheter, which is shaped as needed to receive other components for forming vascular access devices. Catheter 10 comprises a primary conduit 12, which is tubing in its as-extruded form. At a distal end, a tip 14 is formed by a tipping process. At a proximal end, a flange 16 is formed as needed for receipt of other components including but not limited to catheter adapters. Exemplary vascular access devices may include a needle further to the catheter for access to blood vessels.

In one or more embodiments, the medical device is in the form of a catheter, an extension, an IV tubing, a catheter adapter, a luer port, a connector body, a device housing, a component thereof, or a combination thereof. In some embodiments, the catheter comprises a peripherally inserted central catheter (PICC), a peripheral intravenous catheter (PIVC), or a central venous catheter (CVC). In some embodiments, controlled release of the ionically bonded active agent prevents blood stream infections and deep vein thrombosis.

In one or more embodiments, the medical device comprises an ionic polymer ionically bonded to an active agent. The ionic polymer is selected from one or more of a cationic polymer, an anionic polymer and a zwitterionic polymer. In some embodiments, the ionic bond between the active agent and the ionic polymer allows non-leaching and/or controlled release of the active agent. Optionally, a nonionic base polymer may also be included in the medical article. In one or more embodiments, the medical device passively reduces thrombus formation and/or bacterial biofilm formation due to ionic repulsion of bacteria, protein, and blood components.

The ionic polymer includes one or more cationic and/or anionic functional group. In some embodiments, the anionic polymer comprises an anionic functional group. In some embodiments, the anionic polymer comprises at least one anionic functional group, at least two anionic functional groups, or at least three anionic functional groups. In some embodiments, the anionic polymer comprises more than one anionic functional group, more than two anionic functional groups, or more than three anionic functional groups. In some embodiments, the cationic polymer comprises a cationic functional group. In some embodiments, the cationic polymer comprises at least one cationic functional group, at least two cationic functional groups, or at least three cationic functional groups. In some embodiments, the cationic polymer comprises more than one cationic functional group, more than two cationic functional groups, or more than three cationic functional groups. In some embodiments, the zwitterionic polymer comprises an anionic functional group and a cationic functional group. In some embodiments, the zwitterionic polymer comprises at least one anionic functional group, at least two anionic functional groups, or at least three anionic functional groups. In some embodiments, the zwitterionic polymer comprises at least one cationic functional group, at least two cationic functional groups, or at least three cationic functional groups. In some embodiments, the zwitterionic polymer comprise more than one anionic functional group, more than two anionic functional groups, or more than three anionic functional groups. In some embodiments, the zwitterionic polymer comprise more than one cationic functional group, more than two cationic functional groups, or more than three cationic functional groups.

In one or more embodiments, the cationic functional group (e.g., a functional group that has an overall positive charge) may comprise any suitable cationic functional group known to the skilled artisan. In one or more embodiments, the cationic functional group is selected from one or more of quaternary ammonium ($—N^+(R^1)(R^2)(R^3)$), phosphonium ($—P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl. In some embodiments, the ionic polymer is a cationic polymer that does not include a quaternary ammonium group. In other words, in one or more embodiments, the cationic polymer includes one or more cationic functional group selected from phosphonium ($—P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl.

In other embodiments, the ionic polymer is a cationic polymer that has two or more quaternary ammonium groups ($—N^+(R^1)(R^2)(R^3)$), where the quaternary ammonium groups are different from one another.

In some embodiments, two or more cationic functional groups are present in the cationic polymer or the zwitterionic polymer. The two or more cationic functional groups may be selected from quaternary ammonium ($—N^+(R^1)(R^2)(R^3)$), phosphonium ($—P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl.

In one or more embodiments, the anionic functional group (e.g., a functional group that has an overall negative charge) may comprise any suitable anionic functional group known to the skilled artisan. In some embodiments, the anionic functional group comprises one or more of carboxylate ($—COO^-$), sulfonate ($—SO_3^-$), organosulfate ($—O—SO_3^-$), organophosphate ($—O—PO_3^-R^1$ or $—O—PO_3^{2-}$), phenolate ($—C_6H_4—O^-$), and thiolate ($—S^-$), where $R^1$ comprises hydrogen, halogen, alkyl, and aryl.

In one or more specific embodiments, the ionic polymer is an anionic polymer. The anionic polymer may comprise any suitable anionic polymer known to the skilled artisan. In one or more embodiments, the anionic polymer includes a carboxylate ($—COO^-$) functional group. In one or more embodiments, the anionic polymer is selected from the group consisting of carboxylated polyurethane (Becton, Dickinson and Company) and poly(ethylene-co-methacrylic acid) copolymer (e.g., ionomer under the commercial name Surlyn™).

In other embodiments, the anionic polymer includes a sulfonate ($—SO_3^-$) functional group. In other embodiments, the anionic polymer is selected from the group consisting of sulfonated polyurethane (Becton, Dickinson and Company) and perfluorosulfonic acid/polytetrafluoroethylene copolymer (e.g., ionomer under the commercial name Nafion™).

In one or more embodiments, the ionic polymer is a zwitterionic polymer, containing both cationic and anionic functional groups. In some embodiments, the zwitterionic polymer comprises two or more functional groups selected from carboxylate ($—COO^-$), sulfonate ($—SO_3^-$), organosulfate ($—O—SO_3^-$), organophosphate ($—O—PO_3^-R^1$ or $—O—PO_3^{2-}$), phenolate ($—C_6H_4—O^-$), thiolate ($—S^-$), quaternary ammonium ($—N^+(R^1)(R^2)(R^3)$), phosphonium ($—P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl.

In one or more embodiments, the ionic polymer is ionically bonded to an active agent. The active agent may be any suitable active agent known to the skilled artisan. In embodiments wherein the ionic polymer is an anionic polymer, the active agent is a cationic active agent. In embodiments where the ionic polymer is a cationic polymer, the active agent is an anionic active agent. In embodiments where the ionic polymer is a zwitterionic polymer, the active agent may be an anionic active agent or a cationic active agent, or both. In one or more embodiments, the active agent is selected from one or more of an anionic active agent and a cationic active agent. In some embodiments, the cationic active agent may be selected from one or more of chlorhexidine acetate, chlorhexidine gluconate, silver sulfadiazine, benzalkonium chloride, cetylpyridinium chloride, a quaternary ammonium-containing biocide, a guanidine-containing biocide, a cationic antimicrobial polymer, an antimicrobial peptide or peptide-mimics, an antifouling phospholipid or phospholipid-mimics, and derivatives thereof. In some embodiments, the anionic active agent may be selected from one or more of cloxacillin salt, cefoxitin salt, cefazolin salt, penicillin salt, heparin salt, and derivatives thereof. In addition, the skilled artisan will recognize that anionic and/or cationic biocides and anticoagulants of either small molecules or macromolecules can also be used for bonding with cationic and/or anionic functional groups of the ionic polymer.

In one or more embodiments, the medical device releases or is configured to release the active agent in a range of from 4 hours to 90 days. In some embodiments, the medical device releases or is configured to release the active agent over a span of at least 4 hours, at least 8 hours, at least 12 hours, at least 24 hours, at least 48 hours, at least 72 hours, at least 96 hours, at least 120 hours, or at least 144 hours. In some embodiments, the medical device releases or is configured to release the active agent over a span of at least 3 days, at least 7 days, at least 14 days, at least 21 days, at least 30 days, at least 60 days, or at least 90 days.

In one or more embodiments, the medical device comprises an optional nonionic base polymer. In some embodiments, the nonionic base polymer is included in the medical device. In other embodiments, the nonionic base polymer is not included in the medical device. The non-ionic base polymer may comprise any suitable nonionic polymer known to the skilled artisan. In some embodiments, the nonionic base polymer comprises one or more of polyurethane, copolyester, polyolefin, polyvinyl chloride, polycarbonate, acrylic-based copolymer, acetal copolymer, cellulose acetate propionate, acrylonitrile butadiene styrene copolymer, high impact polystyrene, thermoplastic elastomer, synthetic rubber, and silicone elastomer.

In one or more embodiments, a coating including the ionically bonded ionic polymer and the active agent is coated on a body of the medical device. In some embodiments, the coating comprises one or more ionic polymers ionically bonded to one or more active agents. In some embodiments, the coating also includes one or more nonionic base polymers. In some embodiments, the coating is formed by co-dissolving an ionic polymer and an active agent in a solvent system to form an ionic bond between the ionic polymer and the active agent. In some embodiments, the solvent system is optimized to prevent damage to the medical device during the coating process. In some embodiments, the solvent system is optimized such that flashing off of solvents after coating of the medical device results in a final surface coating layer with a controlled coating thickness.

The solvent system for the coating may be any suitable solvent system known to the skilled artisan. In one or more embodiments, the solvent system dissolves both the ionic polymer and the active agent. In one or more embodiments, the solvent system does not cause damage to the medical device substrate during the coating process. In one or more embodiments, the solvent system may be flashed off after coating. In one or more embodiments, the solvent system includes methyl ethyl ketone, tetrahydrofuran, acetone, ethyl formate, methyl formate, 1,3-dioxolane, ethyl acetate, 2-propanol, ethanol, methanol, or mixtures thereof.

In some embodiments, polymer carriers containing at least one ionic polymer can be co-dissolved with at least one active agent in a solvent system to form an ionic bond between the ionic polymer and the active agent. In some embodiments, polymer carriers containing at least one ionic polymer can be co-dissolved with more than one active agent in a solvent system to form an ionic bond between the ionic polymer and the active agent. The coating can then be applied to the surface of the medical device or medical device component.

In some embodiments, the body of the device includes one or more ionic polymers, and the body of the device is imbibed with one or more active agents. In some embodiments, the body of the device may also comprise one or more nonionic base polymers. In some embodiments, imbibing may result in loading of the active agent onto the medical device or medical device component by diffusion in addition to ionic bonding.

In one or more embodiments, the medical device comprises a compounded mixture. In some embodiments, the compounded mixture comprises the ionic polymer and the active agent. In some embodiments, the compounded mixture comprises the one or more ionic polymers ionically bonded to the one or more active agents. In some embodiments, the compounded mixture further comprises one or more nonionic base polymers. In one or more embodiments, the compounded mixture can be molded or extruded into medical devices or medical device components.

In one or more embodiments, the medical device comprises at least one excipient. In some embodiments, the at least one excipient is selected from one or more of thermal stabilizers, light stabilizers, anti-blocking agents, antioxidants, antistatic agents, impact modifiers, reinforcing agents, flame retardants, mold release agents, blowing agents, colorants, radiopaque fillers, lubricating agents, and the like. In some embodiments, the medical device may comprise an excipient in an amount in the range of from 0.01 to 50% w/w.

Another aspect of the disclosure relates to methods of manufacturing medical devices. In one or more embodiments, the method comprises ionically bonding the ionic polymer and the active agent, and, optionally, the nonionic base polymer. The ionic bonding can be achieved by any suitable technique known in the art. Non-limiting examples of suitable techniques include a bulk mixing technique and an imbibing technique. In some embodiments, the bulk mixing technique comprises a solvent mixing technique and a thermal compounding technique.

In one or more embodiments, the body of the device includes the ionic polymer and ionically bonding involves imbibing the body of the medical device with the active agent. In some embodiments, the body of the device also includes the nonionic base polymer. In some embodiments, the body of the device also includes the excipient. In one or more embodiments, the body of the device includes the ionic polymer in an amount of greater than or equal to: 0.01% w/w, 0.1% w/w, 0.5% w/w, 1% w/w, 1.5% w/w, 2% w/w, 3% w/w, 4% w/w, 5% w/w, 10% w/w, 25% w/w, 50% w/w, 75% w/w, or 100% w/w. In one or more embodiments, the body of the device includes the ionic polymer in an amount of less than or equal to: 100% w/w, 75% w/w, 50% w/w, 25% w/w, 10% w/w, 8.0% w/w, 6.0% w/w, 4% w/w, 2% w/w, or 1.0% w/w. In one or more embodiments, the body of the device includes the ionic polymer in an amount ranging from greater than or equal to 0.01 to less than or equal to 100% w/w, and all values and subranges therebetween, including greater than or equal to 0.5 to less than or equal to 75% w/w, greater than or equal to 1 to less than or equal to 50% w/w, and all values and subranges there between; including: greater than or equal to: 0.01% w/w, 0.1% w/w, 0.5% w/w, 1% w/w, 1.5% w/w, 2% w/w, 3% w/w, 4% w/w, 5% w/w, or 10% w/w to less than or equal to: 100% w/w, 75% w/w, 50% w/w, or 25% w/w. In some embodiments, the body of the device includes the ionic polymer for bonding of active agents and advantageously does not require priming (e.g., chemical or plasma treatments) of the device. Accordingly, in some embodiments, when the body of the device includes ionic functionalities, the medical device manufacturing process is simplified, and conversion costs are significantly reduced. As used herein, the term "conversion cost" refers to the cost required to load the device with the active agent. In some embodiments, imbibing advantageously provides a medical device where the active agent is ionically bonded on a surface of the medical device and in the body of the device. In one or more embodiments, imbibing provides continuous and long-term supply of the active agent from the device. In one or more embodiments, the medical device comprising the ionic polymer is effective to passively reduce thrombus formation and/or bacterial biofilm without imbibing treatment. In one or more embodiments, passive reduction of thrombus formation and/or bacterial biofilm of the ionic polymer is due to ionic repulsion of bacteria, protein, and blood components.

In some embodiments, the method further comprises pre-swelling the body of the device. In some embodiments, the method further comprises deionizing the ionic polymer. In some embodiments, an ionic bond between the ionic polymer and the active agent is formed using the imbibing technique. Accordingly, in some embodiments, the imbibing technique includes deionizing the ionic polymer prior to imbibing the body of the device in a solution of the active agent. In some embodiments, the imbibing technique includes pre-swelling the body of the device before deionizing the ionic polymer and imbibing the body of the device in a solution of the active agent.

In some embodiments, process parameters for imbibing method may be tuned to optimize loading and elution of the active agent. Accordingly, in some embodiments, the process parameters include process temperatures, process time, a concentration of the active agent, a selection of the solvent system, or combinations thereof.

In some embodiments, ionically bonding the ionic polymer and the active agent involves preparing a polymer formulation including the active agent. In some embodiments, the polymer formulation comprises the ionic polymer and the active agent. In some embodiments, the polymer formulation further comprises nonionic base polymer. In one or more embodiments, the polymer formulation comprises the ionic polymer in an amount of greater than or equal to: 0.01% w/w, 0.1% w/w, 0.5% w/w, 1% w/w, 1.5% w/w, 2% w/w, 3% w/w, 4% w/w, 5% w/w, 10% w/w, 25% w/w, 50% w/w, 75% w/w, or 99.9% w/w. In one or more embodiments, the polymer formulation comprises the ionic polymer in an amount of less than or equal to: 99.9% w/w, 75% w/w, 50% w/w, 25% w/w, 10% w/w, 8.0% w/w, 6.0% w/w, 4% w/w, 2% w/w, or 1.0% w/w. In one or more embodiments, the polymer formulation comprises the ionic polymer in an amount ranging from greater than or equal to 0.01 to less than or equal to 99.9% w/w, and all values and subranges therebetween, including greater than or equal to 0.5 to less than or equal to 75% w/w, greater than or equal to 1 to less than or equal to 50% w/w, and all values and subranges there between; including: greater than or equal to: 0.01% w/w, 0.1% w/w, 0.5% w/w, 1% w/w, 1.5% w/w, 2% w/w, 3% w/w, 4% w/w, 5% w/w, or 10% w/w to less than or equal to: 99.9% w/w, 75% w/w, 50% w/w, or 25% w/w. In one or more embodiments, the polymer formulation comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w, or 75% w/w. In one or more embodiments, the polymer formulation comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the polymer formulation comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to: 0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w.

In one or more embodiments, preparing the polymer formulation may include compounding the ionic polymer and active agent, and, optionally, the nonionic base polymer to form an ionically bonded compounded mixture. In one or more embodiments, the compounded mixture comprises the ionic polymer in an amount of greater than or equal to: 0.01% w/w, 0.1% w/w, 0.5% w/w, 1% w/w, 1.5% w/w, 2% w/w, 3% w/w, 4% w/w, 5% w/w, 10% w/w, 25% w/w, 50% w/w, 75% w/w, or 99.9% w/w. In one or more embodiments, the compounded mixture comprises the ionic polymer in an amount of less than or equal to: 99.9% w/w, 75% w/w, 50% w/w, 25% w/w, 10% w/w, 8.0% w/w, 6.0% w/w, 4% w/w, 2% w/w, or 1.0% w/w. In one or more embodiments, the compounded mixture comprises the ionic polymer in an amount ranging from greater than or equal to 0.01 to less than or equal to 99.9% w/w, and all values and subranges therebetween, including greater than or equal to 0.5 to less than or equal to 75% w/w, greater than or equal to 1 to less than or equal to 50% w/w, and all values and subranges there between; including: greater than or equal to: 0.01% w/w, 0.1% w/w, 0.5% w/w, 1% w/w, 1.5% w/w, 2% w/w, 3% w/w, 4% w/w, 5% w/w, or 10% w/w to less than or equal to: 99.9% w/w, 75% w/w, 50% w/w, or 25% w/w. In one or more embodiments, the compounded mixture comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w, or 75% w/w. In one or more embodiments, the compounded mixture comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the compounded mixture comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to: 0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w. In some embodiments, compounding advantageously provides a medical device where the active agent is ionically bonded not only on a surface of the medical device but also in the body of the device, thus resulting in continuous and long-term supply of the active agent from the device.

In some embodiments, compounding of the polymer formulation is processed through a twin-screw compounder. Accordingly, in some embodiments, a ratio of one or more of the ionic polymer, the active agent, the nonionic base polymer, and the excipient can be controlled and adjusted by a gravimetric multiple-feeder system. The mixture (conveying through multiple heating and mixing zones) can be continuously passed through a die, a quench tank, and is subsequently cut into regular-sized pellets by a puller-pelletizer. The pellets of the compounded polymer formulation can be used for molding and/or extrusion to form medical devices or medical device components. In some embodiments, the twin-screw compounder process conditions are optimized to achieve uniform mixing of the active agent in the polymer formulation. In some embodiments, uniform mixing is correlated to a desirable elution profile of the active agent from the medical device. In some embodiments, the process parameters of the twin-screw compounder include zone temperatures, screw design, and screw revolutions per minute (RPM). In some embodiments, the method further comprises molding and/or extruding the compounded polymer formulation into the medical device. In some embodiments, the medical device is molded and/or extruded by injection molding and/or extrusion technique.

In one or more embodiments, preparing the polymer formulation may include solvent-mix the ionic polymer and active agent, and, optionally, the nonionic base polymer to form an ionically bonded coating formulation. In one or more embodiments, the coating formulation comprises the ionic polymer in an amount of greater than or equal to: 0.01% w/w, 0.1% w/w, 0.5% w/w, 1% w/w, 1.5% w/w, 2% w/w, 3% w/w, 4% w/w, 5% w/w, 10% w/w, 25% w/w, 50% w/w, 75% w/w, or 99.9% w/w. In one or more embodiments, the coating formulation comprises the ionic polymer in an amount of less than or equal to: 99.9% w/w, 75% w/w, 50% w/w, 25% w/w, 10% w/w, 8.0% w/w, 6.0% w/w, 4% w/w, 2% w/w, or 1.0% w/w. In one or more embodiments, the coating formulation comprises the ionic polymer in an amount ranging from greater than or equal to 0.01 to less than or equal to 99.9% w/w, and all values and subranges therebetween, including greater than or equal to 0.5 to less than or equal to 75% w/w, greater than or equal to 1 to less than or equal to 50% w/w, and all values and subranges there between; including: greater than or equal to: 0.01% w/w, 0.1% w/w, 0.5% w/w, 1% w/w, 1.5% w/w, 2% w/w, 3% w/w, 4% w/w, 5% w/w, 10% w/w, or 25% w/w to less than or equal to: 99.9% w/w, 75% w/w, or 50% w/w. In one or more embodiments, the coating formulation comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w or 75% w/w. In one or more embodiments, the coating formulation comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the coating formulation comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to: 0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w. In some embodiments, the method further comprises applying the coating

EXAMPLES

Example 1

Preparing Samples

Table 1 lists the non-ionic (control) polymers and ionic polymers used in this work. Both ribbon sheet and one-lumen tubing configurations were prepared and tested.

TABLE 1

| ID | Polymer Material | Material Source | Ionic Property of Polymer | Sample Musical Form |
|---|---|---|---|---|
| C1 | Regular polyurethane PU-A | Becton, Dickinson and Company | Non-ionic (Control) | Ribbon sheet with thickness of 0.007-0.010 in. |
| C2 | Low density polyethylene | Commercial resin DOW ™ 5004I | Non-ionic (Control) | Ribbon sheet with thickness of 0.007-0.010 in. |
| C3 | Regular polyurethane PU-A compounding with 20 wt. % of BaSO₄ | Becton, Dickinson and Company | Non-ionic (Control) | Ribbon sheet with thickness of 0.007-0.010 in. |
| R1 | Carboxylated polyurethane CP-2 | Becton, Dickinson and Company | Anionic content of ~0.167 mmol/g; in acid form | Ribbon sheet with thickness of 0.007-0.010 in. |
| R2 | Carboxylated polyurethane CP-3 | Becton, Dickinson and Company | Anionic content of ~0.391 mmol/g; in acid form | Ribbon sheet with thickness of 0.007-0.010 in. |
| R3 | Sulfonated polyurethane SP-2 | Becton, Dickinson and Company | Anionic content of ~0.199 mmol/g; in sodium salt form | Ribbon sheet with thickness of 0.007-0.010 in. |
| R4 | Sulfonated polyurethane SP-5 | Becton, Dickinson and Company | Anionic content of ~0.273 mmol/g; in sodium salt form | Ribbon sheet with thickness of 0.007-0.010 in. |
| R5 | Carboxylated polyurethane CP-2 compounding with 20 wt. % of BaSO₄ | Becton, Dickinson and Company | Anionic content of ~0.134 mmol/g; in acid form | Ribbon sheet with thickness of 0.007-0.010 in. |
| R6 | Sulfonated polyurethane SP-5 compounding with 20 wt. % of BaSO₄ | Becton, Dickinson and Company | Anionic content of ~0.218 mmol/g; in sodium salt form | Ribbon sheet with thickness of 0.007-0.010 in. |
| R7 | Poly(ethylene-co-methacrylic acid) copolymer | Commercial resin Surlyn ™ 8940 ionomer | Anionic content of ~1.74 mmol/g; in acid and sodium salt mixed form | Ribbon sheet with thickness of 0.007-0.010 in. |
| R8 | Perfluorosulfonic acid/polytetrafluoroethylene copolymer | Commercial Nafion ™ 117 membrane sheet | Anionic content of ~0.91 mmol/g; in acid form | Membrane sheet with thickness of 0.007 in. |
| T1 | Carboxylated polyurethane CP-2 (tubing) | Becton, Dickinson and Company | Anionic content of ~0.167 mmol/g; in acid form | One-lumen tubing; OD = 0.058 in.; ID = 0.0449 in.; Wall Thickness = 0.0067 in. |
| T2 | Sulfonated polyurethane SP-5 (tubing) | Becton, Dickinson and Company | Anionic content of ~0.273 mmol/g; in sodium salt form | One-lumen tubing; OD = 0.058 in.; ID = 0.0449 in.; Wall Thickness = 0.0067 in. |
| T3 | Sulfonated polyurethane SP-5 compounding with 20 wt. % of BaSO₄ (tubing) | Becton, Dickinson and Company | Anionic content of ~0.218 mmol/g; in sodium salt form | One-lumen tubing; OD = 0.058 in.; ID = 0.0449 in.; Wall Thickness = 0.0067 in. |
| T4 | Perfluorosulfonic acid/polytetrafluoroethylene copolymer (tubing) | Commercial Nafion ™ tubing | Anionic content of ~0.91 mmol/g; in acid form | One-lumen tubing; OD = 0.072 in.; ID = 0.060 in.; Wall Thickness = 0.0060 in. | formulation onto the surface of medical device or medical device component. In some embodiments, such ionically bonded coating formulation advantageously simplifies the medical device manufacturing process and significantly reduces conversion costs. In some embodiments, coating advantageously allows loading of an active agent onto the surface of traditional medical devices.

In some embodiments, process parameters for coating formulation method may be tuned to optimize loading and elution of the active agent. Accordingly, in some embodiments, the process parameters include process temperatures, process time, ingredient concentrations, a selection of the solvent system, or combinations thereof.

Example 2

Samples C1, C2, R1, R2, R7, R8 and T4 (as listed in Table 1) were tested following below procedures.

Imbibing Sample. Each sample (~5 cm² ribbon sheet or ~5 cm length tubing) was pre-swollen by soaking in 50/50 v/v % of methanol/dioxolane solution (C1, C2, R1, R7, R8 and T4) or 100% methanol (R2) at room temperature for 30 minutes. Each sample was then soaked in 50 mM of Tris-Base buffer solution (90/10 v/v % of methanol/water) at 35° C. for 120 minutes for de-protonation of ionic functionalities. Each sample was then soaked in 10 mL of methanol for 1 minute at room temperature to rinse off the Tris-Base buffer solution. Each sample was then soaked in 10 mL of loading solution. The loading solution comprised an active agent in 30/70 v/v % of methanol/water and used at 37° C. for 24 hours. The active agent comprised chlorhexidine acetate (100 mM)/sodium citrate (1 mM). Each sample was placed on an Orbital Shaker during this loading process. After the loading process, each sample was soaked in 10 mL of methanol for 1 minute at room temperature to rinse off the loading solution. After rinsing, each sample was dried in a fume hood at room temperature overnight to flash off the residue methanol solvent.

Chlorhexidine Elution in Human Serum. Each sample loaded with chlorhexidine, as described above, was soaked in the elution media comprising 60/40 v/v % of human serum/phosphate buffered saline at 37° C. (on Orbital Shaker@150 RPM) for time intervals of 3 hours to 20 days. At each designated time interval, the previous elution media was removed for chlorhexidine elution analysis and quantification by high-performance liquid chromatography (HPLC) and fresh elution media was used for the next time interval. Chlorhexidine elution is defined as the mass of chlorhexidine eluted per unit area of sample in the unit of $\mu g/cm^2$.

Chlorhexidine Post-Elution Extraction. After elution testing, the remaining chlorhexidine in each sample was completely extracted using the extraction media comprising 0.3/70/30 v/v/v % of trifluoroacetic acid/acetonitrile/water at 37° C. for 24 hours (on Orbital Shaker@150 RPM), followed by analysis and quantification of remaining chlorhexidine in each sample by HPLC. The chlorhexidine remaining is defined as the mass of chlorhexidine remained per unit area of sample in the unit of $\mu g/cm^2$.

Chlorhexidine Loading Calculation. Chlorhexidine initial loading on the sample can be calculated by adding total chlorhexidine elution (adding up all elution time points) and the chlorhexidine remain (by post-elution extraction).

Table 2 shows the chlorhexidine initial loading data (average of 3 replicates) of both the control polymers without ionic functionalities and the ionic polymers by the above imbibing approach.

TABLE 2

| ID | Polymer Material | Chlorhexidine Initial Loading ($\mu g/cm^2$) |
|---|---|---|
| C1 | Regular polyurethane PU-A | 65.7 |
| C2 | Low density polyethylene | 53.1 |

TABLE 2-continued

| ID | Polymer Material | Chlorhexidine Initial Loading ($\mu g/cm^2$) |
|---|---|---|
| R1 | Carboxylated polyurethane CP-2 | 353.3 |
| R2 | Carboxylated polyurethane CP-3 | 2658.4 |
| R7 | Poly(ethylene-co-methacrylic acid) copolymer | 234.2 |
| R8 | Perfluorosulfonic acid/ polytetrafluoroethylene copolymer | 4084.3 |
| T4 | Perfluorosulfonic acid/ polytetrafluoroethylene copolymer (tubing) | 5482.3 |

Table 2 shows that control polymers without ionic functionalities (C1 and C2) both exhibited low chlorhexidine loading (only ~50 $\mu g/cm^2$) after imbibing, which is non-bonded free chlorhexidine trapped within the polymer matrix during imbibing. However, ionic polymers (R1, R2, R7, R8 and T4) exhibited much higher chlorhexidine loading after imbibing, due to ionic interactions between the anionic functional group and chlorhexidine.

Table 3 shows the chlorhexidine elution in human serum and remain data (average of 3 replicates) of both the control polymers without ionic functionalities and the ionic polymers.

TABLE 3

| | Chlorhexidine Content ($\mu g/cm^2$) | | | | | | |
|---|---|---|---|---|---|---|---|
| | C1 | C2 | R1 | R2 | R7 | R8 | T4 |
| Elution 0-3 h | 43.4 | 47.0 | 23.6 | 79.8 | 89.7 | 109.0 | 185.0 |
| Elution 3-6 h | 5.9 | 4.1 | 9.0 | 3.8 | 2.8 | 41.9 | 51.7 |
| Elution 6-24 h | 5.8 | 0.9 | 3.5 | 6.2 | 2.6 | 50.6 | 125.5 |
| Elution 24-48 h | 2.5 | 0 | 1.9 | 5.5 | 2.1 | 29.3 | 94.6 |
| Elution 48-72 h | / | / | / | 6.3 | / | / | 49.3 |
| Elution 48-96 h | 3.4 | / | 3.4 | / | / | / | / |
| Elution 48-120 h | / | 0.6 | / | / | 2.9 | 43.8 | / |
| Elution 72-96 h | / | / | / | 5.0 | / | / | 31.1 |
| Elution 96-168 h | 2.8 | / | 2.4 | 7.1 | / | / | 37.3 |
| Elution 120-168 h | / | 0.5 | / | / | 1.1 | 27.3 | / |
| Elution 168-216 h | / | / | / | 5.8 | / | 21.9 | 19.3 |
| Elution 216-336 h | / | / | / | 6.6 | / | 31.0 | 21.7 |
| Elution 336-480 h | / | / | / | 5.9 | / | / | 16.9 |
| Remain | 1.8 | 0 | 309.4 | 2528.6 | 132.9 | 3729.4 | 4849.8 |

Figure 2:
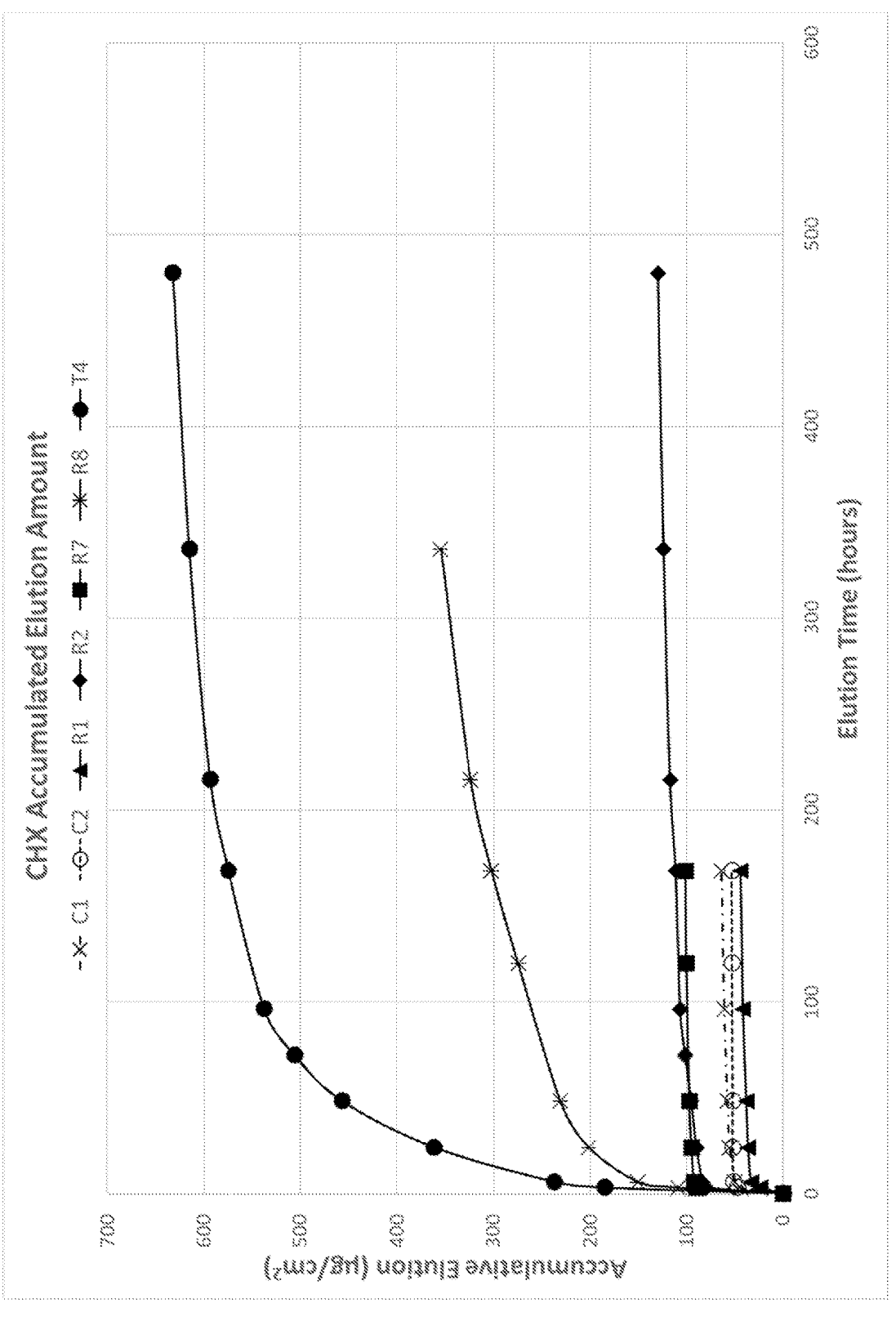
FIG. 2 illustrates an elution profile of a medical device according to one or more embodiments of the disclosure.

FIG. 2 shows the chlorhexidine accumulated elution in human serum over a period of time of both the control polymers without ionic functionalities and the ionic polymers.

Table 3 and FIG. 2 show the chlorhexidine elution profiles of both the control polymers without ionic functionalities and the ionic polymers. For control polymers without ionic functionalities (C1 and C2), majority of loaded chlorhexidine eluted out in the first 24 h, and minimum amount of chlorhexidine left within the polymer matrix after Day 1. Thus, the polymers do not show a controlled release. For ionic polymers (R1, R2, R7, R8 and T4), only small portion of loaded chlorhexidine eluted out in the first 24 h, which presumably to be the non-bonded and/or weakly bonded chlorhexidine trapped within the polymer matrix. The remaining chlorhexidine was ionically bonded within the polymer matrix and showed a slow release.

Example 3

Samples R1, R2, R4, R7, R8 and T4 (as listed in Table 1) were tested following below procedures. Different as Example 2, chlorhexidine acetate (400 mM) in methanol was used as the imbibing solution instead of chlorhexidine acetate (100 mM)/sodium citrate (1 mM) in 30/70 v/v % of methanol/water.

Imbibing Sample. Each sample (~5 cm² ribbon sheet or ~5 cm length tubing) was pre-swollen by soaking in 50/50 v/v % of methanol/dioxolane solution (R1, R7, R8 and T4) or 100% methanol (R2 and R4) at room temperature for 30 minutes. Each sample was then soaked in 50 mM of Tris-Base buffer solution (90/10 v/v % of methanol/water) at 35° C. for 120 minutes for de-protonation of ionic functionalities. Each sample was then soaked in 10 mL of methanol for 1 minute at room temperature to rinse off the Tris-Base buffer solution. Each sample was then soaked in 10 mL of loading solution. The loading solution comprised chlorhexidine acetate (400 mM) in methanol and used at 37° C. for 24 hours. Each sample was placed on an Orbital Shaker during this loading process. After the loading process, each sample was soaked in 10 mL of methanol for 1 minute at room temperature to rinse off the loading solution. After rinsing, each sample was dried in a fume hood at room temperature overnight to flash off the residue methanol solvent.

Chlorhexidine Elution in Human Serum. Each sample loaded with chlorhexidine, as described above, was soaked in the elution media comprising 60/40 v/v % of human serum/phosphate buffered saline at 37° C. (on Orbital Shaker@150 RPM) for time intervals of 3 hours to 21 days. At each designated time interval, the previous elution media was removed for chlorhexidine elution analysis and quantification by high-performance liquid chromatography (HPLC) and fresh elution media was used for the next time interval. Chlorhexidine elution is defined as the mass of chlorhexidine eluted per unit area of sample in the unit µg/cm².

Table 4 shows the chlorhexidine initial loading data (average of 3 replicates) of the ionic polymers by the above imbibing approach.

TABLE 4

| ID | Polymer Material | Chlorhexidine Initial Loading (µg/cm²) |
|---|---|---|
| R1 | Carboxylated polyurethane CP-2 | 2957.1 |
| R2 | Carboxylated polyurethane CP-3 | 6571.5 |
| R4 | Sulfonated polyurethane SP-5 | 1286.7 |
| R7 | Poly(ethylene-co-methacrylic acid) copolymer | 958.1 |
| R8 | Perfluorosulfonic acid/ polytetrafluoroethylene copolymer | 3861.9 |
| T4 | Perfluorosulfonic acid/ polytetrafluoroethylene copolymer (tubing) | 5508.7 |

Compared to Table 2, Table 4 shows that using chlorhexidine acetate (400 mM) in methanol as the imbibing solution instead of chlorhexidine acetate (100 mM)/sodium citrate (1 mM) in 30/70 v/v % of methanol/water, chlorhexidine loading of perfluorosulfonic acid/polytetrafluoroethylene copolymer (R8 and T4) does not change significantly; however chlorhexidine loading of carboxylated polyurethane (R1 and R2) and poly(ethylene-co-methacrylic acid) copolymer (R7) significantly increased.

Table 5 shows the chlorhexidine elution in human serum and remain data (average of 3 replicates) of the ionic polymers.

TABLE 5

| | Chlorhexidine Content (µg/cm²) | | | | | |
|---|---|---|---|---|---|---|
| | R1 | R2 | R4 | R7 | R8 | T4 |
| Elution 0-3 h | 75.3 | 132.3 | 108.0 | 403.4 | 80.2 | 259.0 |
| Elution 3-6 h | 31.2 | 62.8 | 34.5 | 20.2 | 26.7 | 68.7 |
| Elution 6-24 h | 47.6 | 119.5 | 89.6 | 7.2 | 51.1 | 129.5 |
| Elution 24-48 h | 33.6 | 88.9 | 67.9 | 3.6 | 35.8 | 88.8 |
| Elution 48-72 h | 24.0 | 62.5 | 47.8 | / | / | 39.7 |
| Elution 48-120 h | / | / | / | 4.0 | 60.8 | / |
| Elution 72-96 h | 21.7 | 56.0 | 46.9 | / | / | 21.8 |
| Elution 96-168 h | 39.7 | 103.8 | 76.7 | / | / | 44.4 |
| Elution 120-168 h | / | / | / | 1.3 | 33.7 | / |
| Elution 168-216 h | / | / | / | / | 28.0 | 20.4 |
| Elution 168-240 h | 30.4 | 83.5 | / | / | / | / |
| Elution 216-336 h | / | / | / | / | 44.1 | 44.6 |
| Elution 240-336 h | 35.8 | 86.7 | / | / | / | / |
| Elution 336-408 h | 21.7 | 54.6 | / | / | / | / |
| Elution 336-480 h | / | / | / | / | / | 33.7 |
| Elution 408-504 h | 25.9 | 64.7 | / | / | / | / |
| Remain | 2570.2 | 5656.2 | 815.4 | 518.3 | 3504.5 | 4758.2 |

Chlorhexidine Post-Elution Extraction. After elution testing, the remaining chlorhexidine in each sample was completely extracted using the extraction media comprising 0.3/70/30 v/v/v % of trifluoroacetic acid/acetonitrile/water at 37° C. for 24 hours (on Orbital Shaker@150 RPM), followed by analysis and quantification of remaining chlorhexidine in each sample by HPLC. The chlorhexidine remaining is defined as the mass of chlorhexidine remained per unit area of sample in the unit of µg/cm².

Chlorhexidine Loading Calculation. Chlorhexidine initial loading on the sample can be calculated by adding total chlorhexidine elution (adding up all elution time points) and the chlorhexidine remain (by post-elution extraction).

Figure 3:
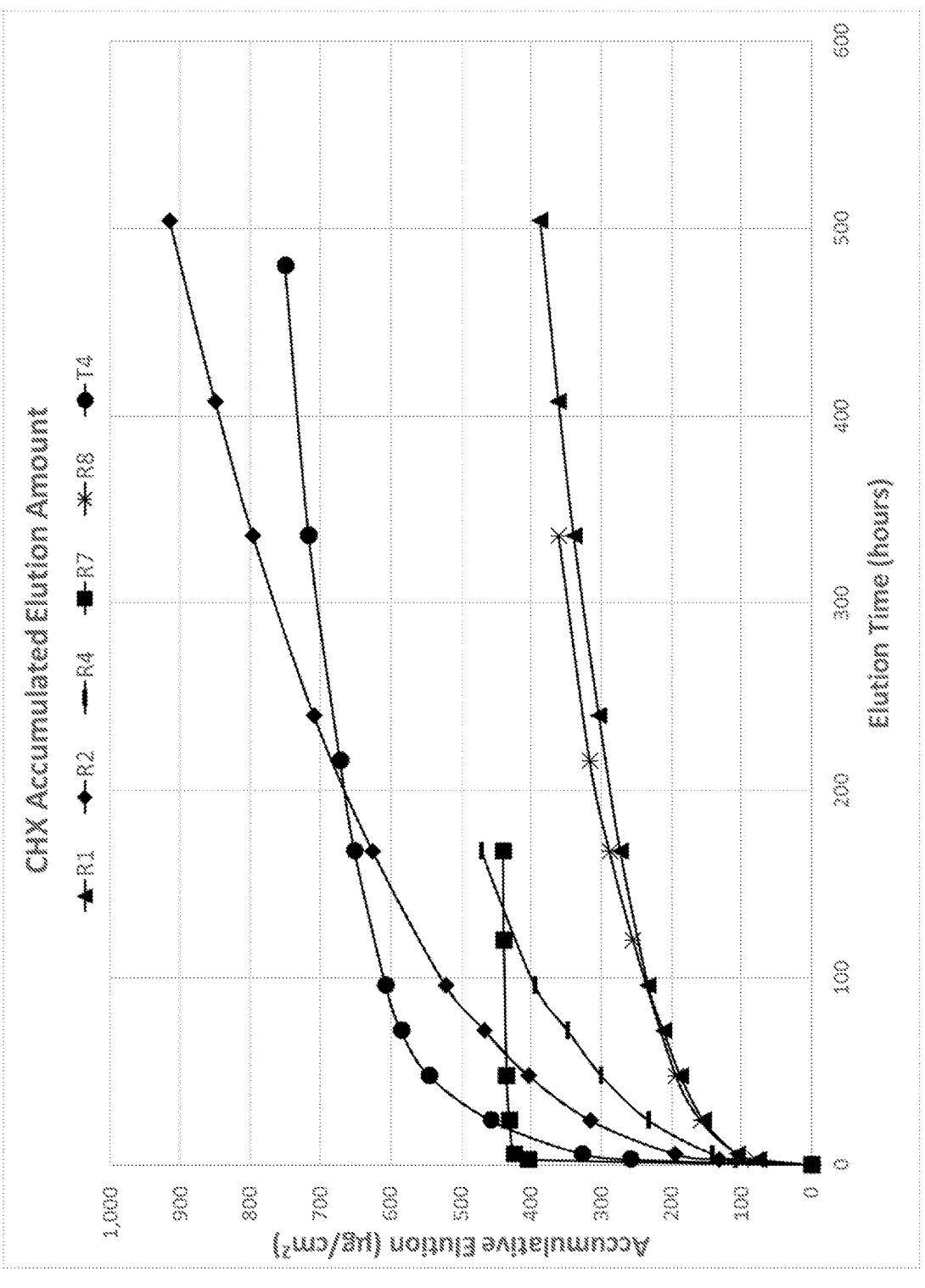
FIG. 3 illustrates an elution profile of a medical device according to one or more embodiments of the disclosure.

FIG. 3 shows the chlorhexidine accumulated elution in human serum over a period of time of the ionic polymers.

Table 5 and FIG. 3 show the chlorhexidine elution profiles of the ionic polymers. Data show that using chlorhexidine acetate (400 mM) in methanol as the imbibing solution instead of chlorhexidine acetate (100 mM)/sodium citrate (1 mM) in 30/70 v/v % of methanol/water, chlorhexidine elution of perfluorosulfonic acid/polytetrafluoroethylene copolymer (R8 and T4) does not change significantly; however, chlorhexidine elution of carboxylated polyurethane (R1 and R2) significantly improved.

Example 4

Samples C3, R1, R2, R3, R4, R5, R6, T1, T2 and T3 (as listed in Table 1) were tested following below procedures. Different as Example 3, pre-swelling and de-protonation steps were not applied, and samples were directly imbibed in the solution of chlorhexidine acetate (400 mM) in methanol.

Imbibing Sample. Each sample (~5 cm² ribbon sheet or ~5 cm length tubing) was soaked in 10 mL of loading solution. The loading solution comprised chlorhexidine acetate (400 mM) in methanol and used at 37° C. for 24 hours. Each sample was placed on an Orbital Shaker during this loading process. After the loading process, each sample was soaked in 10 mL of methanol for 1 minute at room temperature to rinse off the loading solution. After rinsing, each sample was dried in a fume hood at room temperature overnight to flash off the residue methanol solvent.

Chlorhexidine Elution in Human (or Bovine) Serum. Each sample loaded with chlorhexidine, as described above, was soaked in the elution media comprising 60/40 v/v % of human (or bovine) serum/phosphate buffered saline at 37° C. (on Orbital Shaker@150 RPM) for time intervals of 3 hours to 60 days. At each designated time interval, the previous elution media was removed for chlorhexidine elution analysis and quantification by high-performance liquid chromatography (HPLC) and fresh elution media was used for the next time interval. Chlorhexidine elution is defined as the mass of chlorhexidine eluted per unit area of sample in the unit of μg/cm².

Chlorhexidine Post-Elution Extraction. After elution testing, the remaining chlorhexidine in each sample was completely extracted using the extraction media comprising 0.3/70/30 v/v/v % of trifluoroacetic acid/acetonitrile/water at 37° C. for 24 hours (on Orbital Shaker@150 RPM), followed by analysis and quantification of remaining chlorhexidine in each sample by HPLC. The chlorhexidine remaining is defined as the mass of chlorhexidine remained per unit area of sample in the unit of μg/cm².

Chlorhexidine Loading Calculation. Chlorhexidine initial loading on the sample can be calculated by adding total chlorhexidine elution (adding up all elution time points) and the chlorhexidine remain (by post-elution extraction).

Table 6 shows the chlorhexidine initial loading data (average of 3 replicates) of both the control polymer without ionic functionalities and the ionic polymers by the above imbibing approach.

TABLE 6

| ID | Polymer Material | Chlorhexidine Initial Loading (μg/cm²) |
|---|---|---|
| C3 | Regular polyurethane PU-A compounding with 20 wt. % of BaSO₄ | 142.4 |
| R1 | Carboxylated polyurethane CP-2 | 2044.4 |
| R2 | Carboxylated polyurethane CP-3 | 6697.2 |
| R3 | Sulfonated polyurethane SP-2 | 1787.5 |
| R4 | Sulfonated polyurethane SP-5 | 3067.1 |
| R5 | Carboxylated polyurethane CP-2 compounding with 20 wt. % of BaSO₄ | 1787.3 |
| R6 | Sulfonated polyurethane SP-5 compounding with 20 wt. % of BaSO₄ | 2027.2 |
| T1 | Carboxylated polyurethane CP-2 (tubing) | 1149.6 |
| T2 | Sulfonated polyurethane SP-5 (tubing) | 1840.8 |
| T3 | Sulfonated polyurethane SP-5 compounding with 20 wt. % of BaSO₄ (tubing) | 1466.4 |

Similar as the observations in Table 2, Table 6 shows that the control polymer without ionic functionalities (C3) exhibited low chlorhexidine loading after imbibing, which is nonbonded free chlorhexidine trapped within the polymer matrix during imbibing. However, ionic polymers (R1, R2, R3, R4, R5, R6, T1, T2 and T3) exhibited much higher chlorhexidine loading after imbibing, due to ionic interactions between the anionic functional group and chlorhexidine. Since these ionic polymers are all polyurethane-based materials, higher anionic content generally resulted in higher chlorhexidine loading. Table 6 also shows that even without pre-swelling and de-protonation steps, very desirable chlorhexidine loading was still achieved with a single step imbibing process. Thus, the imbibing process can be significantly simplified. In addition, Table 6 shows that for the same ionic polymer, tubing configuration (i.e., T1, T2 and T3) exhibited lower chlorhexidine loading compared to ribbon sheet configuration (i.e., R1, R4 and R6) due to the thinner tubing wall compared to the thickness of the ribbon sheet, resulting in less mass of material and less ionic content per unit area of sample for tubing vs. ribbon sheet.

Table 7 shows the chlorhexidine elution in human (or bovine) serum and remain data (average of 3 replicates) of both the control polymer without ionic functionalities and the ionic polymers.

TABLE 7

| | Chlorhexidine Content (μg/cm²) | | | | |
|---|---|---|---|---|---|
| Elution Medium | C3 Bovine Serum | R1 Bovine Serum | R2 Human Serum | R3 Bovine Serum | R4 Bovine Serum |
| Elution 0-3 h | 4.8 | 52.1 | 98.1 | 101.4 | 85.5 |
| Elution 3-6 h | 1.3 | 12.4 | 57.5 | 31.0 | 20.2 |
| Elution 6-24 h | 4.6 | 22.7 | 129.9 | 65.3 | 104.2 |
| Elution 24-48 h | 3.8 | 16.0 | 105.7 | 42.0 | 87.3 |
| Elution 48-72 h | 2.4 | / | 76.7 | / | 55.6 |
| Elution 48-144 h | / | 31.9 | / | 72.6 | / |
| Elution 72-96 h | 2.0 | / | 68.6 | / | 46.7 |
| Elution 96-168 h | / | / | 127.5 | / | / |
| Elution 96-192 h | 4.6 | / | / | / | 125.1 |
| Elution 144-168 h | / | 5.9 | / | 15.4 | / |
| Elution 168-216 h | / | 13.7 | / | 27.3 | / |
| Elution 168-240 h | / | / | 97.3 | / | / |
| Elution 192-240 h | 2.4 | / | / | / | 59.4 |
| Elution 216-288 h | / | 16.8 | / | 32.1 | / |
| Elution 240-336 h | 2.5 | / | 112.2 | / | 95.4 |
| Elution 288-336 h | / | 10.5 | / | 19.8 | / |
| Elution 336-408 h | / | / | 69.7 | / | 77.8 |

TABLE 7-continued

| Elution | | | | | |
|---|---|---|---|---|---|
| Elution 408-504 h | / | / | 88.8 | / | 69.3 |
| Elution 504-576 h | / | / | / | / | 53.2 |
| Elution 576-672 h | / | / | / | / | 67.9 |
| Elution 672-720 h | / | / | / | / | 37.8 |
| Elution 720-840 h | / | / | / | / | 57.8 |
| Elution 840-912 h | / | / | / | / | 53.8 |
| Elution 912-1008 h | / | / | / | / | 55.4 |
| Elution 1008-1080 h | / | / | / | / | 37.7 |
| Elution 1080-1176 h | / | / | / | / | 40.7 |
| Elution 1176-1224 h | / | / | / | / | 20.8 |
| Elution 1224-1272 h | / | / | / | / | 17.7 |
| Elution 1272-1368 h | / | / | / | / | 22.6 |
| Elution 1368-1440 h | / | / | / | / | 19.7 |
| Remain | 114.0 | 1862.3 | 5665.2 | 1380.7 | 1755.5 |

| | Chlorhexidine Content ($\mu g/cm^2$) | | | | |
|---|---|---|---|---|---|
| | R5 | R6 | T1 | T2 | T3 |
| Elution Medium | Bovine Serum | Bovine Serum | Bovine Serum | Bovine Serum | Bovine Serum |
| Elution 0-3 h | 31.7 | 91.1 | 29.2 | 101.0 | 100.7 |
| Elution 3-6 h | 5.9 | 19.7 | 3.0 | 31.1 | 29.5 |
| Elution 6-24 h | 33.1 | 93.1 | 12.9 | 70.8 | 51.6 |
| Elution 24-48 h | 21.9 | 70.2 | 8.0 | 56.0 | 49.7 |
| Elution 48-72 h | 13.6 | 44.1 | 7.0 | 39.1 | 36.1 |
| Elution 72-96 h | 10.3 | 35.2 | / | / | / |
| Elution 72-168 h | / | / | 21.2 | 87.4 | 96.9 |
| Elution 96-192 h | 33.7 | 103.6 | / | / | / |
| Elution 168-240 h | / | / | 12.9 | 53.9 | 49.6 |
| Elution 192-240 h | 14.2 | 44.2 | / | / | / |
| Elution 240-336 h | 24.0 | 74.7 | 11.5 | 52.2 | 43.9 |
| Elution 336-408 h | 17.0 | 54.3 | 8.9 | 39.6 | 33.9 |
| Elution 408-504 h | 16.3 | 42.8 | 15.5 | 61.8 | 44.9 |
| Elution 504-576 h | 12.9 | 30.9 | 10.0 | 38.8 | 29.5 |
| Elution 576-672 h | 14.1 | 34.0 | / | 47.1 | 28.3 |
| Elution 672-720 h | 7.3 | 17.7 | / | / | / |
| Elution 672-744 h | / | / | / | 32.0 | 19.8 |
| Elution 720-840 h | 13.7 | 24.8 | / | / | / |
| Elution 744-840 h | / | / | / | 31.9 | 19.3 |
| Elution 840-912 h | / | 31.9 | / | / | / |
| Elution 912-1008 h | / | 29.8 | / | / | / |
| Elution 1008-1080 h | / | 19.0 | / | / | / |
| Elution 1080-1176 h | / | 18.1 | / | / | / |
| Elution 1176-1224 h | / | 9.2 | / | / | / |
| Elution 1224-1272 h | / | 7.2 | / | / | / |
| Elution 1272-1368 h | / | 7.5 | / | / | / |
| Elution 1368-1440 h | / | 7.3 | / | / | / |
| Remain | 1517.7 | 1117.0 | 1009.4 | 1092.2 | 832.7 |

Figure 4:
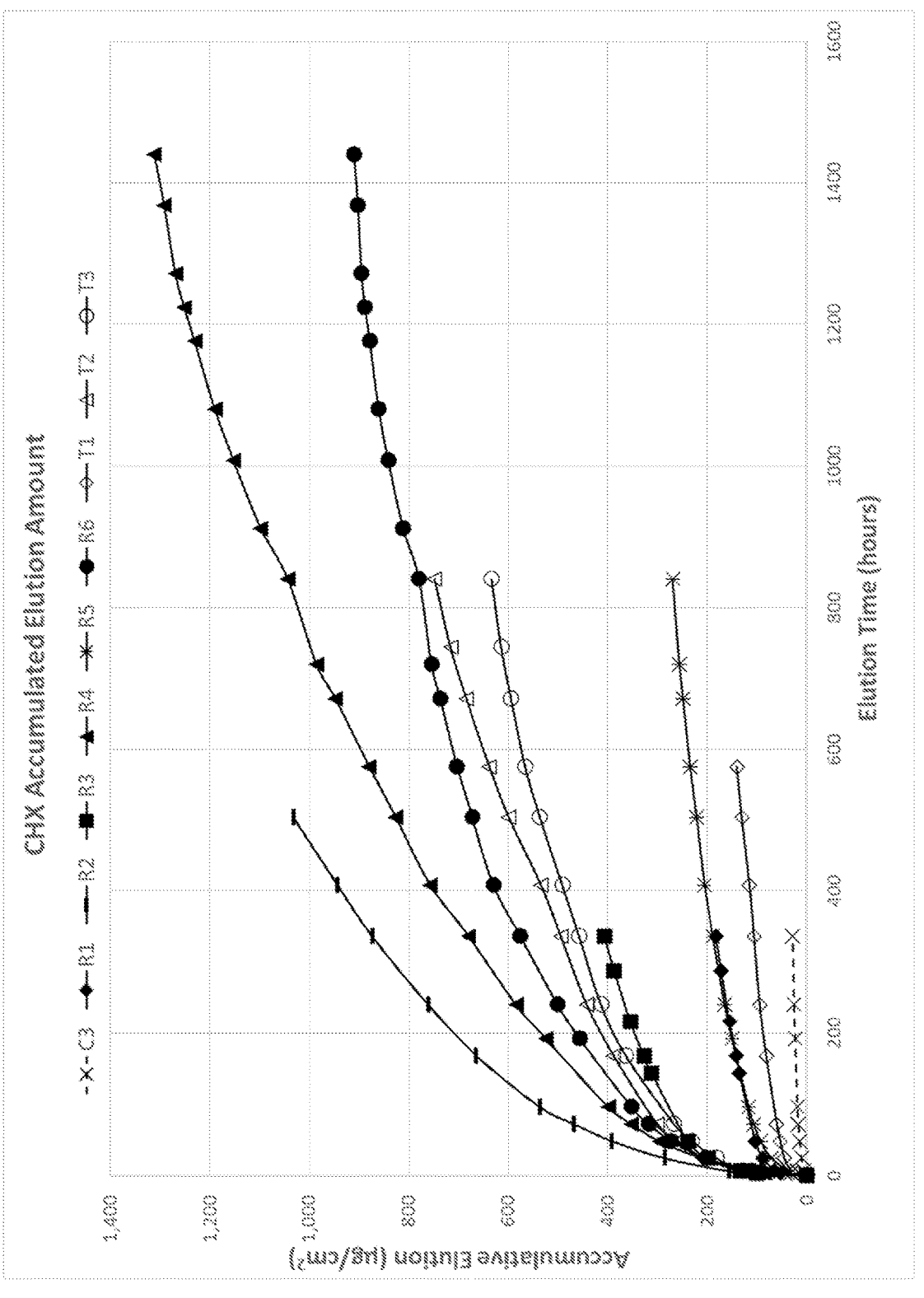
FIG. 4 illustrates an elution profile of a medical device according to one or more embodiments of the disclosure.

FIG. 4 shows the chlorhexidine accumulated elution in human (or bovine) serum over a period of time of both the control polymer without ionic functionalities and the ionic polymers.

Table 7 and FIG. 4 show the chlorhexidine elution profiles of both the control polymer without ionic functionalities and the ionic polymers. Similar as previously observed, the control polymer without ionic functionalities (C3) does not show a controlled release due to the low chlorhexidine loading. However, ionic polymers (R1, R2, R3, R4, R5, R6, T1, T2 and T3) showed very desirable and controlled release profiles up to 60 days. Since these ionic polymers are all polyurethane-based materials, higher anionic content generally resulted in higher chlorhexidine loading as well as higher chlorhexidine daily release. Data also show that even without pre-swelling and de-protonation steps, very desirable and controlled chlorhexidine release profiles were still achieved with a single step imbibing process. Thus, the imbibing process can be significantly simplified. For the same ionic polymer, tubing configuration (i.e., T1, T2 and T3) exhibited lower chlorhexidine daily release compared to ribbon sheet configuration (i.e., R1, R4 and R6) due to the thinner tubing wall compared to the thickness of the ribbon sheet, resulting in less mass of material, less ionic content and less chlorhexidine loading per unit area of sample for tubing vs. ribbon sheet.

Example 5

Antimicrobial Efficacy

Sample C1 (as listed in Table 1) was used as the control. Samples R1, R2, R3, R4 and R6 (as listed in Table 1) were imbibed following procedures in Example 4 for chlorhexidine loading.

Imbibing Sample. Each sample coupon (R1, R2, R3, R4 and R6, 1.5 cm×1.5 cm) was soaked in 5 mL of loading solution. The loading solution comprised chlorhexidine acetate (400 mM) in methanol and used at 37° C. for 24 hours. Each sample was placed on an Orbital Shaker during this loading process. After the loading process, each sample was soaked in 5 mL of methanol for 1 minute at room temperature to rinse off the loading solution. After rinsing, each sample was dried in a fume hood at room temperature overnight to flash off the residue methanol solvent.

Antimicrobial Testing. The antimicrobial efficacy of the imbibed coupons (R1, R2, R3, R4 and R6) against *Candida albicans* (yeast), Coagulase Negative *Staphylococcus epi-*

21

*dermidis* (gram-positive), and *Klebsiella pneumoniae* (gram-negative) were tested after 1, 3, 7, and 14 days of preconditioning. The testing method can quantitatively measure the microbial colonization on and around the sample coupons (both control and imbibed test coupons). The coupon samples were assembled into the testing devices and sterilized by ethylene oxide prior to testing.

The preconditioning of coupon samples was performed up to 14 days using 60% Human Serum (HS) in phosphate buffered saline (PBS) at 37±2° C. with constant agitation and the preconditioning solution was changed daily with fresh sterile 60% HS in PBS.

After 1, 3, 7, and 14 days of preconditioning in HS, the coupon samples (both control and imbibed test coupons) were challenged with 3 different microbial organisms: i) *Candida albicans* (yeast, —$1.0 \times 10^5$ CFU/device) in 20% Mueller Hinton Broth (MHB) in Butterfield's Phosphate Buffer, ii) Coagulase Negative *Staphylococcus epidermidis* (gram-positive, —$1.0 \times 10^5$ CFU/device) in 20% Nutrient Broth (NB) in Butterfield's Phosphate Buffer, and iii) *Klebsiella pneumoniae* (gram-negative, —$1.0 \times 10^5$ CFU/device) in 10% Nutrient Broth (NB) in Butterfield's Phosphate

22 ally diluting and plating on prepared Tryptic Soy Agar (TSA) plates. The plates were incubated at 37±2° C. and counted after approximately 16-24 hours of incubation. Data was evaluated as total CFU recovered/device. $\text{Log}_{10}$ Reduction is compared to control sample (C1) counts.

$$\text{Log}_{10}CFU/\text{device} = \text{Log}_{10}\left(CFU/\text{device} + 1\right) \qquad \text{Equation (1)}$$

$$\text{Log}_{10}\text{Reduction} = \qquad \text{Equation (2)}$$

$$\left(\text{Log}_{10}CFU/\text{device control}\right) - \left(\text{Log}_{10}CFU/\text{device test}\right)$$

$$\% \text{ Kill} = \left(\left(\left(CFU/\text{device control}\right) - \left(CFU/\text{device test}\right)\right) \div \qquad \text{Equation (3)}\right.$$

$$\left(CFU/\text{device control}\right)\right) \times 100$$

Table 8 shows a summary of the antimicrobial testing results for both planktonic and biofilm reductions of all three microbial organisms after 1, 3, 7, and 14 days of HS preconditioning.

TABLE 8

| | | Candida albicans | | | | Staphylococcus epidermidis | | | | Klebsiella pneumoniae | | | |
| | | Planktonic | | Biofilm | | Planktonic | | Biofilm | | Planktonic | | Biofilm | |
| Preconditioning | VS. C1 | $\text{Log}_{10}$ Reduction | % Kill | $\text{Log}_{10}$ Reduction | % Kill | $\text{Log}_{10}$ Reduction | % Kill | $\text{Log}_{10}$ Reduction | % Kill | $\text{Log}_{10}$ Reduction | % Kill | $\text{Log}_{10}$ Reduction | % Kill |
|---|---|---|---|---|---|---|---|---|---|---|---|---|---|
| After 1-day HS | R1 | 7.74 | 100 | 5.02 | 100 | 8.33 | 100 | 6.27 | 100 | 8.99 | 100 | 4.83 | 100 |
| preconditioning | R2 | 7.74 | 100 | 5.02 | 100 | 8.33 | 100 | 6.27 | 100 | 8.99 | 100 | 5.88 | 100 |
| | R3 | 7.74 | 100 | 5.02 | 100 | 8.33 | 100 | 5.35 | 100 | 8.99 | 100 | 2.95 | 99.89 |
| | R4 | 7.74 | 100 | 4.11 | 99.99 | 8.33 | 100 | 5.62 | 100 | 8.99 | 100 | 5.88 | 100 |
| | R6 | 7.74 | 100 | 4.74 | 100 | 8.33 | 100 | 5.78 | 100 | 8.99 | 100 | 5.88 | 100 |
| After 3-day HS | R1 | 7.80 | 100 | 4.03 | 100 | 8.42 | 100 | 5.15 | 100 | 9.04 | 100 | 3.30 | 100 |
| preconditioning | R2 | 7.80 | 100 | 4.90 | 100 | 8.42 | 100 | 6.16 | 100 | 9.04 | 100 | 4.65 | 100 |
| | R3 | 7.80 | 100 | 4.38 | 100 | 8.42 | 100 | 3.49 | 100 | 9.04 | 100 | 6.15 | 100 |
| | R4 | 7.80 | 100 | 4.74 | 100 | 8.42 | 100 | 5.14 | 100 | 9.04 | 100 | 2.95 | 100 |
| | R6 | 7.80 | 100 | 5.10 | 100 | 8.42 | 100 | 3.87 | 100 | 9.04 | 100 | 1.75 | 98 |
| After 7-day HS | R1 | 5.76 | 100 | 2.51 | 100 | 7.87 | 100 | 5.45 | 100 | 8.05 | 100 | 4.61 | 100 |
| preconditioning | R2 | 7.81 | 100 | 3.85 | 100 | 7.87 | 100 | 5.45 | 100 | 9.02 | 100 | 4.96 | 100 |
| | R3 | 7.81 | 100 | 3.01 | 100 | 7.87 | 100 | 5.45 | 100 | 9.02 | 100 | 6.50 | 100 |
| | R4 | 7.81 | 100 | 4.65 | 100 | 7.87 | 100 | 5.45 | 100 | 9.02 | 100 | 6.50 | 100 |
| | R6 | 7.81 | 100 | 4.23 | 100 | 7.87 | 100 | 5.45 | 100 | 9.02 | 100 | 6.50 | 100 |
| After 14-day HS | R1 | 0.87 | 87 | 0.86 | 86 | 8.11 | 100 | 5.51 | 100 | 3.90 | 100 | 0.93 | 88 |
| preconditioning | R2 | 7.78 | 100 | 5.21 | 100 | 8.11 | 100 | 5.51 | 100 | 9.07 | 100 | 4.42 | 100 |
| | R3 | 0.70 | 80 | 0.48 | 67 | 8.11 | 100 | 5.51 | 100 | 6.87 | 100 | 2.95 | 100 |
| | R4 | 4.60 | 100 | 3.46 | 100 | 8.11 | 100 | 5.51 | 100 | 9.07 | 100 | 3.97 | 100 |
| | R6 | 7.78 | 100 | 4.95 | 100 | 8.11 | 100 | 5.51 | 100 | 9.07 | 100 | 3.56 | 100 |

Buffer. The challenge was incubated at 37±2° C. for 24 hours with constant agitation. Testing was performed in triplicate for each microbial organism challenge at each time point.

Planktonic Recovery. After 24 hours of microbial challenge, the challenge media were neutralized with D/E Neutralizing Broth and the surviving colony forming units (CFUs) were quantified by serially diluting and plating on prepared Tryptic Soy Agar (TSA) plates. The plates were incubated at 37±2° C. and counted after approximately 16-24 hours of incubation. Data was evaluated as total CFU recovered/device. $\text{Log}_{10}$ Reduction is compared to control sample (C1) counts.

Biofilm Recovery. After 24 hours of microbial challenge, the coupon samples were rinsed with sterile saline and placed in D/E Neutralizing Broth. Then, the coupon samples were sonicated to recover biofilms adhered to the coupons. The recovered biofilm suspensions were quantified by seri- Table 8 shows that after 1, 3, and 7 days of HS preconditioning, all these imbibed ionic polymers (R1, R2, R3, R4 and R6) presented very desirable antimicrobial performance (both planktonic and biofilm reductions) against all three microbial organisms due to their desirable chlorhexidine elution at Day 1, Day 3, and Day 7. After 14 days of HS preconditioning, high ionic content imbibing samples (R2, R4 and R6) still presented very desirable antimicrobial performance (both planktonic and biofilm reductions) against all three microbial organisms due to their high chlorhexidine loading as well as continued high chlorhexidine elution at Day 14; low ionic content imbibing samples (R1 and R3) still presented desirable antimicrobial performance (both planktonic and biofilm reductions) against *Staphylococcus epidermidis*, but start to loose antimicrobial efficacy against *Candida albicans* and/or *Klebsiella pneumoniae* due to their relatively lower chlorhexidine loading as well as relatively lower chlorhexidine elution at Day 14.

Overall, results show that this technology is very efficient for long-term antimicrobial applications (e.g., indwell catheters).

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of manufacturing a medical device, the method comprising:

ionically bonding an ionic polymer and an active agent, and, optionally, a nonionic base polymer to form a body of the medical device, the body including the ionic polymer ionically bonded to the active agent, the ionic polymer comprising one or more of an anionic polymer, a cationic polymer, and a zwitterionic polymer, wherein the anionic polymer comprises a functional group selected from one or more of carboxylate ($—COO—$), sulfonate ($—SO_3—$), organosulfate ($—O—SO_3—$), organophosphate ($—O—PO_3—R^1$ or $—O—PO_3{}^{2}—$), phenolate ($—C_6H_4—O—$), and thiolate ($—S—$), wherein the cationic polymer comprises a functional group selected from one or more of phosphonium ($—P^+(R^1)(R^2)(R^3)$), imidazolium, pyridinium, sulfonium, guanidinium, thiazolium, and quinolinium, or wherein the cationic polymer comprises two or more functional groups selected from quaternary ammonium ($—N^+(R^1)(R^2)(R^3)$), phosphonium ($—P^+(R^1)(R^2)(R^3)$), imidazolium, pyridinium, sulfonium, guanidinium, thiazolium, and quinolinium, wherein the zwitterionic polymer comprises two or more functional groups selected from carboxylate ($—COO—$), sulfonate ($—SO_3—$), organosulfate ($—O—SO_3—$), organophosphate ($—O—PO_3—R^1$ or $—O—PO_3{}^{2}—$), phenolate ($—C_6H_4—O—$), thiolate ($—S—$), quaternary ammonium ($—N^+(R^1)(R^2)(R^3)$), phosphonium ($—P^+(R^1)(R^2)(R^3)$), imidazolium, pyridinium, sulfonium, guanidinium, thiazolium, and quinolinium, and wherein $R^1$, $R^2$, and $R^3$ independently comprise hydrogen, halogen, alkyl, and aryl.

2. The method of claim 1, further comprising coating the ionically bonded ionic polymer and the active agent, and, optionally, the nonionic base polymer, on the body of the medical device.

3. The method of claim 1, further comprising compounding the ionically bonded ionic polymer and the active agent, and, optionally, the nonionic base polymer to form a compounded mixture.

4. The method of claim 1, wherein the body of the medical device comprises the ionic polymer and, optionally, the nonionic base polymer, and ionically bonding comprises imbibing the body of the medical device with the active agent.

5. The method of claim 1, wherein ionically bonding comprises preparing a polymer formulation comprising the ionic polymer, the active agent, and, optionally, the nonionic base polymer.

6. The method of claim 1, wherein the active agent comprises one or more of an anionic active agent and a cationic active agent.

7. The method of claim 1, wherein the active agent is released over a span of at least 24 hours.

8. The method of claim 1, wherein the active agent is released over a span of at least three days.

9. The method of claim 1, wherein the active agent is released over a span of at least seven days.

10. The method of claim 1, wherein the active agent is released over a span of at least thirty days.

11. The method of claim 1, wherein the active agent comprises a cationic active agent.

12. The method of claim 1, wherein the active agent is selected from the group consisting of an antimicrobial agent, an antithrombotic agent, or combinations thereof.

13. The method of claim 11, wherein the cationic active agent comprises one or more of chlorhexidine acetate, chlorhexidine gluconate, silver sulfadiazine, benzalkonium chloride, cetylpyridinium chloride, a quaternary ammonium-containing biocide, a guanidine-containing biocide, a cationic antimicrobial polymer, an antimicrobial peptide or peptide-mimics, an antifouling phospholipid or phospholipid-mimics, and derivatives thereof.

14. The method of claim 1, wherein the medical device is in the form of a catheter, an extension, an IV tubing, a catheter adapter, a luer port, a connector body, a device housing, a component thereof, or a combination thereof.

15. The method of claim 1, further comprising adding at least one excipient.

16. The method of claim 15, wherein the at least one excipient is selected from the group consisting of thermal stabilizers, light stabilizers, anti-blocking agents, antioxidants, antistatic agents, impact modifiers, reinforcing agents, flame retardants, mold release agents, blowing agents, colorants, radiopaque fillers, and the like.

17. The method of claim 1, wherein the ionic polymer is selected from the group consisting of carboxylated polyurethane, poly(ethylene-co-methacrylic acid) copolymer, sulfonated polyurethane and perfluorosulfonic acid/polytetrafluoroethylene copolymer.

* * * * *